United States Patent
Van Rens et al.

(10) Patent No.: US 12,390,164 B2
(45) Date of Patent: **\*Aug. 19, 2025**

(54) SENSING DEVICE AND METHOD FOR MULTIPLE REMOTE SENSORS

(71) Applicant: KONINKLIJKE PHILIPS N.V., Eindhoven (NL)

(72) Inventors: Antonia Cornelia Van Rens, Nuenen (NL); Amine Mounaim, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 18/623,142

(22) Filed: Apr. 1, 2024

(65) Prior Publication Data
US 2024/0245358 A1 Jul. 25, 2024

Related U.S. Application Data

(63) Continuation of application No. 16/763,279, filed as application No. PCT/EP2018/081154 on Nov. 14, 2018, now Pat. No. 11,944,457.

(30) Foreign Application Priority Data

Nov. 15, 2017 (EP) .................... 17201782

(51) Int. Cl.
*A61B 5/00* (2006.01)
*A61B 5/277* (2021.01)
*A61B 8/06* (2006.01)

(52) U.S. Cl.
CPC ............ *A61B 5/6851* (2013.01); *A61B 5/277* (2021.01); *A61B 5/6852* (2013.01);
(Continued)

(58) Field of Classification Search
CPC ..... A61B 5/6851; A61B 5/277; A61B 5/6852; A61B 5/7225; A61B 8/06; A61B 2505/05;
(Continued)

(56) References Cited

U.S. PATENT DOCUMENTS

| | | |
|---|---|---|
| 2005/0024066 A1 | 2/2005 | Chandler |
| 2005/0148832 A1 | 7/2005 | Reghabi |
| 2018/0235545 A1 | 8/2018 | Barakat |

FOREIGN PATENT DOCUMENTS

| | | |
|---|---|---|
| WO | 200154576 A1 | 8/2001 |
| WO | 2004021044 A1 | 3/2004 |

(Continued)

OTHER PUBLICATIONS

International Search Report & Written Opinion of PCT/EP2018/081154, dated Feb. 4, 2019.
(Continued)

*Primary Examiner* — Scott M. Getzow

(57) ABSTRACT

A sensor device comprises at least two sensors at the end of a shaft (such as a guidewire or catheter). One sensor uses signals in a first frequency range and a first voltage range and the other sensor uses signals in a second frequency range different to the first frequency range and a second voltage range different to the first voltage range. The first sensor is shorted based on frequency analysis, thereby to prevent the first sensor being exposed to signals associated with the second sensor. This enables the two sensors to be driven by the same shared pair of wires along the shaft, with automatic selection of the suitable sensor.

12 Claims, 3 Drawing Sheets

(52) U.S. Cl.
CPC .............. *A61B 5/7225* (2013.01); *A61B 8/06* (2013.01); *A61B 2505/05* (2013.01); *H03F 2200/129* (2013.01); *H03F 2200/171* (2013.01); *H03F 2203/45528* (2013.01)

(58) Field of Classification Search
CPC ......... H03F 2200/129; H03F 2200/171; H03F 2203/45528; H03F 3/45475; G01D 21/02
See application file for complete search history.

(56) References Cited

FOREIGN PATENT DOCUMENTS

| | | |
|---|---|---|
| WO | 2013061272 A1 | 5/2013 |
| WO | 2016050972 A1 | 4/2016 |

OTHER PUBLICATIONS

Kolling, Arjan et al "Two-Lead Multiplex System for Sensor Array Applications", Sensors and Actuators, vol. 17, No. 3-4, May 17, 1989, pp. 623-628.

Ji, Jin et al "An Ultraminiature CMOS Pressure Sensor for a Multiplexed Cardiovascular Catheter", IEEE Transactions on Electron Devices, vol. 39, No. 10, Oct. 1, 1992, pp. 2260-2267.

SENSING DEVICE AND METHOD FOR MULTIPLE REMOTE SENSORS

CROSS-REFERENCE TO PRIOR APPLICATIONS

This application is a continuation of U.S. application Ser. No. 16/763,279, filed May 12, 2020, now U.S. Pat. No. 11,944,457, which is the U.S. National Phase application under 35 U.S.C. § 371 of International Application No. PCT/EP2018/081154, filed on Nov. 14, 2018, which claims the benefit of European Patent Application No. 17201782.4, filed on Nov. 15, 2017. These applications are hereby incorporated by reference herein.

FIELD OF THE INVENTION

This invention relates to devices that incorporate sensing functionality at the remote tip of a shaft such as a catheter.

BACKGROUND OF THE INVENTION

Minimally invasive surgery method require the implementation of sensors for imaging or for physiological parameter monitoring at the tip of guidewires and catheters.

However, the very limited size of these instruments poses an important challenge in integrating the required sensing functionality. Micro-electromechanical system (MEMS) sensors can be integrated with ASIC technology and enable advanced imaging and/or sensing functionality in a very small area.

The interconnect between the in-vivo sensors and the ex-vivo sensor system has to be optimized as well, basically meaning the number of system wires has to be minimized. A low wire count is important due to the limited space available to route the wires. For example, a typical outer diameter of a coronary guidewire is 360 μm. A low wire count is also important as it simplifies the soldering or other bonding of the system wires to the sensor die.

One known sensor solution is a capacitive pressure sensor for use in a medical guidewire. The pressure sensing guidewire is known as a pressure wire. The capacitive pressure sensing device is monolithically integrated with its readout circuit.

FIG. 1 shows this arrangement, which comprises a sensor control system 10 at one (proximal) end of a shaft 12 and a pressure sensor 14 at the other (distal) end.

A pair of electrical wires 16 run along the shaft. The solution only uses only two electrical interface signals; one ground signal on one of the wires and one signal that carries the sensor DC supply voltage (e.g. 2.5V) and also carries a frequency modulated current as the sensor signal. This modulation is read by the sensor control system 10.

The connection scheme based on two signals is significant as it simplifies the soldering and bonding of the system wires to the miniaturized sensor die. The signals are transferred via two conductive ribbons from the distal end to the proximal end of the shaft, e.g. catheter.

It has been proposed to integrate a pressure sensor and a flow sensor in a single guidewire. A known flow sensor is based on Doppler ultrasound and uses a conventional ultrasound transducer element that is placed forward looking in the guidewire. Preferably, the solution should use two wires as well as shown in FIG. 2. The two wires 16 connect to both the pressure sensor 14 and the flow sensor 15 in parallel.

The flow sensor 15 is a high voltage sensor whereas the pressure sensor is a low voltage sensor. This means they cannot easily be driven by the same supply. Instead, there is a need for a switching solution that selects between the high voltage sensor and the low voltage sensor but ideally without the need for an extra wire. This is challenging, as the low voltage sensor will break down when not protected adequately from the high voltage sensor signals. This becomes even more challenging when the high voltage sensor is stimulated using bi-polar pulses as may be the case for an ultrasound transducer sensor.

As an example, it is possible to integrate a high voltage transistor switch in the low voltage readout circuit. When applying a high voltage signal, the switch opens to isolate the low voltage sensor from the voltage carried by the signal wires 16. However, such a switch will only protect the low voltage readout circuit for one signal polarity. For the opposite signal polarity, a parasitic PN junction may start conducting and the isolation function will not then be effective.

There remains a need for a solution which enables high voltage and low voltage sensors to be supplied by a common pair of electrical wires, with the low voltage sensor being protected from the high voltages of the high voltage sensor. In particular, this protection should be achieved without requiring any additional control wire.

The article "Two-Lead Multiplex System for Sensor Array Applications", Arjan Kolling et. al., Sensors and Actuators, vol. 17, no. 3-4, 17 May 1989, pages 623-628 (XP026575381), discloses a two-wire sensor multiplexing approach, in which sensor chips are connected sequentially to the shared pair of leads. The sensor chips are all the same.

SUMMARY OF THE INVENTION

The invention is defined by the claims.

According to examples in accordance with an aspect of the invention, there is provided a sensor device comprising:
a shaft;
a pair of electrical wires running along the shaft;
a sensing head at a distal end of the shaft connected to the pair of electrical wires, wherein the sensing head comprises:
  a first sensor that is associated with signals carried by the pair of electrical wires in a first frequency range and a first voltage range;
  a second sensor that is associated with signals carried by the pair of electrical wires in a second frequency range different to the first frequency range and a second voltage range different to the first voltage range; and
a shorting circuit comprising a shorting switch and a frequency-dependent filter circuit for controlling the switching of the shorting switch, wherein the shorting circuit is adapted to short the first sensor based on at least frequency by closing the shorting switch when signals in the second frequency range are present on the pair of electrical wires, thereby to prevent the first sensor being exposed to signals associated with the second sensor.

This device enables two sensors that make use of different voltages and frequencies to be driven by a shared pair of connection wires, with automatic selection of the suitable sensor. In particular, the first sensor is shorted to protect it from the signals that result from the use of the second sensor. The invention is based on implementing this shorting function based on different frequency and/or voltage amplitude characteristics of the signals associated with the two sensors, so that for example the first sensor is shorted when signals are present which are only characteristic of the second sensor. The shorting provides a protection function in that it forces a zero volt difference across the shorted sensor.

Note that a sensor may be "associated with" signals of a particular frequency or voltage range either because the sensing function generates such signals or because sensor drive signals provided to the sensor have those characteristics, or both. Simultaneous driving and readout for the one activated sensor is for example possible by using current driving and voltage sensing or voltage driving and current sensing. For a pressure sensor, the supply voltage for example provides driving of the sensor and the sensing is based on the current. Driving and sensing may instead be time-sequential.

A flow sensor may for example be based on a pulsed wave Doppler ultrasound principle.

The invention may be applied to any sensor types, as long as the two (or more) sensor types can be distinguished by the frequency and/or voltage amplitude characteristics of the signals that result on one or both of the electrical wires.

The shorting of the first sensor does not short the signal wires but rather shorts the inputs to the first sensor. For example, a resistor may be in series with the shorting switch between the two signal wires.

The shorting circuit comprises a shorting switch and a frequency-dependent filter circuit for controlling the switching of the shorting switch. When large amplitude signals that have frequency components unique to the second sensor are present, the first sensor is shorted. The switching may thus be based on voltage amplitude as well as frequency.

The second frequency range is for example higher than the first frequency range. In this case, the second sensor is a high frequency sensor, in which use of the second sensor is stimulated with large amplitude high frequency signals on at least one of the wires. The first frequency range may include DC, and may comprise a narrow frequency band above DC, or a wider frequency band as long as the top of the frequency band is below the frequency range of the second sensor if frequency separation only is used.

The DC component (needed for the first sensor) may be present no matter which sensor is active. In this case, the switch will start conducting only when the high frequency signals with sufficient amplitude are detected.

Note that an alternative is to detect the DC characteristic of the signals associated with the first sensor. If no such DC component is present for the second sensor, the absence of the DC component may be used as the condition for switching the shorting circuit.

The shorting circuit for example comprises a shorting switch and a high pass filter circuit for closing the shorting switch when signals in the second frequency range are present. The high pass filter looks for signals characteristic to the second sensor. The high pass filter circuit may be formed using a low pass filter and a comparator, or a low pass filter and a transistor.

The second voltage range is for example higher than first voltage range. Thus, the first sensor may need protection from the voltages in the second range that are characteristic of operation of the second sensor.

The first sensor for example comprises a pressure sensor. It may comprise a capacitive sensor based on DC driving, with modulation of a sensor current to provide encoding of a pressure value. Indeed, the first sensor generally may provide an output signal as a modulated current on the pair of electrical wires. Even though the modulated current with not be a DC signal, the amplitude may be insufficient to trigger the frequency-dependent control. The switching is thus based on both frequency and amplitude control.

The second sensor may comprise a flow sensor. Thus, the device enables in-vivo pressure and flow rate monitoring. The flow sensor may comprise an ultrasound sensor. This is for example activated by providing high voltage high frequency pulses on one of the pair of wires, and reading resulting echo signals also provided as return pulses.

The shaft for example comprises a catheter or guidewire.

The device may also comprise a sensor control system at the opposite end of the shaft to the sensor head, wherein the sensor control system comprises:
  means for providing a DC voltage on the second of the pair of electrical wires;
  a ground connection for a first one of the pair of electrical wires;
  a first readout amplifier for reading out a modulated current on the second of the pair of electrical wires;
  a driving unit for providing a drive voltage on the second of the pair of electrical wires in the second frequency range; and
  a second readout amplifier for reading out a sensor signal on the second of the pair of electrical wires in the second frequency range.

One wire is grounded, so that the other carries the signals in the first or second voltage range and the first or second frequency range.

In one arrangement, the second readout amplifier provides the second voltage range that is used by the shorting circuit to disable and protect operation of the first sensor.

In an alternative arrangement, the DC voltage is used by the shorting circuit to allow operation of the first sensor. When this DC voltage is provided, the activation of the second sensor (by providing a high voltage drive voltage using the driving unit) is then not carried out.

The driving unit and the second readout amplifier are used for operation of the second sensor.

The means for providing the DC voltage may be implemented by the first readout amplifier.

The first readout amplifier may further comprises a low pass filter or a band pass filter for selecting signals of the first sensor. Thus, even if a response of the second sensor is picked up, it can be filtered out.

The invention also provides a method of controlling a sensor device, the sensor device comprising a shaft, a pair of electrical wires running along the shaft and a sensing head at a distal end of the shaft connected to the pair of electrical wires, wherein the method comprises:
  operating a first sensor of the sensor head resulting in signals carried by the pair of electrical wires in a first frequency range and a first voltage range; and
  operating a second sensor of the sensor head resulting in signals carried by the pair of electrical wires in a second frequency range and a second voltage range;
  wherein the method comprises shorting the first sensor based on at least frequency by detecting when signals in the second frequency range are present on the pair of electrical wires using a frequency-dependent filter circuit, and in response closing a shorting switch thereby to prevent the first sensor being exposed to signals associated with the second sensor.

In this method, a frequency (and optionally also amplitude) based control is used to short the first sensor so that is not exposed to the (higher voltage) signals of the second sensor.

Operation of the first sensor may comprise providing a voltage in the first voltage range and in the first frequency range including DC on one of the pair of electrical wires to drive the first sensor to generate signals. Thus, a signal in a characteristic first voltage range and first frequency range is a drive signal to the sensor rather than the sensor output.

Operation of the second sensor may comprise providing an AC actuation signal in the second voltage range and in the second frequency range on said one of the pair of electrical wires to drive a second sensor of the sensor head to generate signals in said second frequency range. The drive signals and sensing signals may thus be in the second frequency range.

The shorting comprises controlling a shorting switch using a frequency-dependent filter circuit.

The method may comprise pressure sensing with the first sensor and flow sensing with the second sensor.

BRIEF DESCRIPTION OF THE DRAWINGS

Examples of the invention will now be described in detail with reference to the accompanying drawings, in which.

DETAILED DESCRIPTION OF THE EMBODIMENTS

Figure 1:
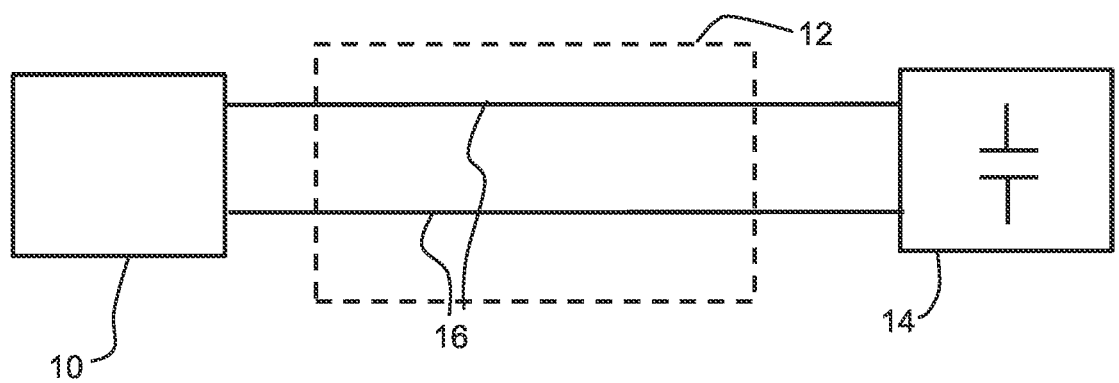
FIG. 1 shows an arrangement having a remote pressure sensor at the end of a shaft.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a sensor device comprising at least two sensors at the end of a shaft (such as a guidewire or catheter). One sensor uses signals in a first frequency range and a first voltage range and the other sensor uses signals in a second frequency range different to the first frequency range and a second voltage range different to the first voltage range. The input to the first sensor is shorted based on frequency and/or voltage amplitude analysis, thereby to prevent the first sensor being exposed to signals associated with the second sensor. This enables the two sensors to be driven by the same shared pair of wires along the shaft, with automatic selection of the suitable sensor.

Figure 2:
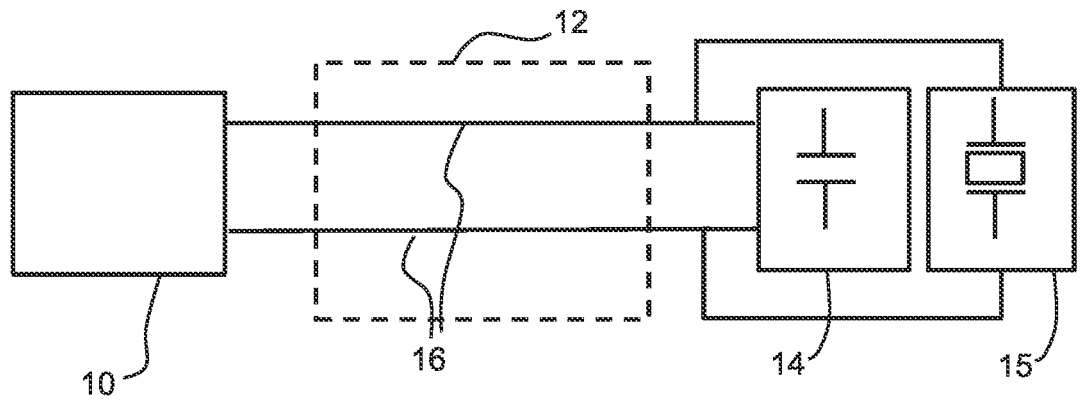
FIG. 2 shows a desired arrangement having a remote pressure sensor and a remote flow sensor at the end of a shaft.
Figure 3:
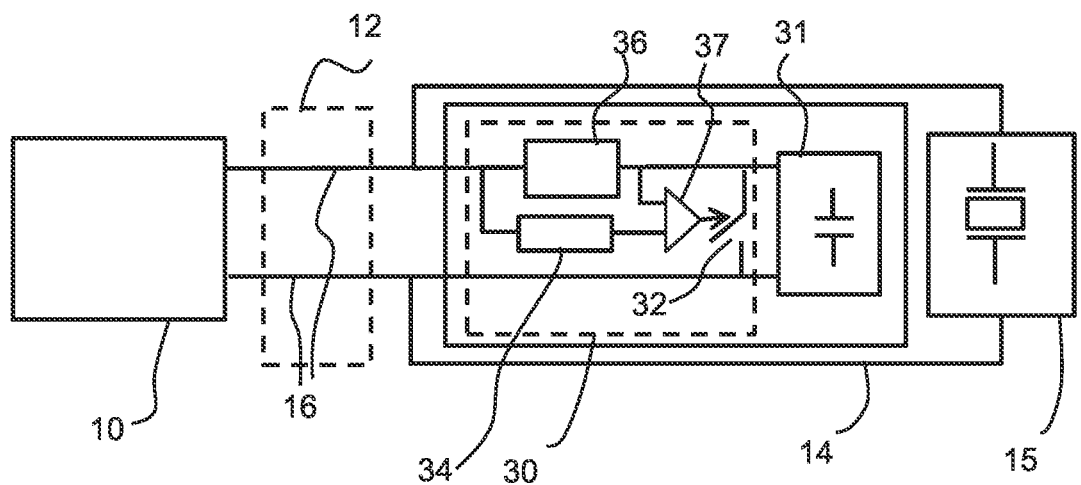
FIG. 3 shows in schematic form a sensor device in accordance with an example of the invention.

FIG. 3 shows in schematic form a sensor device comprising a shaft 12 with a pair of electrical wires 16 running along the shaft as for the example of FIGS. 1 and 2. A sensing head is provided at the distal end of the shaft connected to the pair of electrical wires.

A first sensor 14 is associated with signals carried by the pair of electrical wires 16 in a first frequency range and a first voltage range. The first sensor is for example a low voltage capacitive pressure sensor. It is driven by a low voltage DC drive signal. The first frequency range is thus simply DC or else a range from absolute DC to a cut-off frequency. The pressure sensor is driven by the DC voltage and modulates a current in order to provide a sensing signal. This sensing signal may for example be modulated using amplitude modulation or any other modulation scheme, including a binary pulse width modulation (PWM) of the current, i.e. a sequence of pulses that alternate between two current levels. The modulated current may have a low maximum frequency that is dependent on the signal being sensed, or else it may have a frequency that depends on the switching or sampling used as part of the sensing process. For example, a PWM based current modulation may have a dominant frequency in the kHz range as a result of the PWM switching.

Because of the remaining presence of a DC drive voltage, the "first frequency range" may simply relate to the voltage present, and does not need to take account of the fluctuating current. The cut-off frequency may be below the maximum frequency of the modulated current, or it may be above that frequency as long as it remains below the frequency associated with use of the second sensor. Preferably, the cut-off frequency is above the frequency range of the modulated signal of the first sensor.

A second sensor 15 is associated with signals carried by the pair of electrical wires in a second frequency range different to the first frequency range and a second voltage range different to the first voltage range.

The second frequency range is for example higher than the first frequency range with no overlap. The second sensor is for example a Doppler ultrasound sensor, in which high voltage MHz activation pulses are used to drive the sensor, and (low voltage) MHz echo pulses are returned. The example shown is based on the use of a Doppler ultrasound sensor that does not use a DC voltage bias so that the voltage on the wires has no DC component, but instead is a bipolar pulse stream. There may however be an AC component, for example in an ultrasound system with a DC bias, for example a CMUT collapse voltage.

A shorting circuit 30 is provided for shorting the first sensor 14 based on frequency, thereby to prevent the first sensor being exposed to signals associated with the second sensor. The shorting circuit 30 is provided between the external input of the first sensor and the internal sensor readout circuit 31.

The shorting circuit comprises a switch 32 implemented as a low voltage transistor across the inputs of the circuit 31. When turned on, a limited voltage is present across the circuit elements in the circuit 31. The switch is controlled by a filter circuit 34 so that when the first sensor is being used (the DC drive voltage is present and the high voltage pulses are not present) the switch is not conducting, and when the second sensor is being used (the DC drive voltage may or may not be present, but the high voltage pulses are present) the switch is closed i.e. conductive.

The shorting function is for example integrated into the low voltage sensor readout circuit 31 (typically an application specific integrated circuit, ASIC). A series resistor 36 means that even with the switch 32 closed, a drive voltage can still be provided to the second sensor 15. The high voltage drive signal for the second sensor then appears predominantly across the series resistor but not on the low voltage sensor readout circuit 31.

The filter circuit 34 for example comprises a low pass filter that extracts the low frequency component. This low frequency component is then compared with the original signal (after passing through the resistor 36) by a comparator 37. If the voltage after the resistor 36 is greater than the voltage after the low pass filter 34 by more than a threshold, the shorting switch is closed.

As an alternative, the filter circuit may comprise of a high pass filter that detects the existence of a high frequency signal. If the amplitude of the detected high-frequency signal is larger than a threshold, the shorting switch is closed. A suitable circuit implementation for this is identical to a standard implementation of a power supply clamping circuit that is used for electrostatic discharge (ESD) protection circuits.

Thus, the shorting switch is closed when a significant amount of signal is removed by the low pass filter. Thus, the overall circuit functions as a high pass filter, in that only if there is a significant high frequency component is the shorting switch activated. This has the effect of protecting the low voltage sensor readout circuit 31. This general overall function will be described as a high pass filter function.

There are other ways to implement this overall high pass filter function. For example, the comparator 37 may be replaced with a low voltage PMOS transistor. When the voltage difference exceeds the transistor threshold, the transistor starts conducting. If the input voltage after the resistor 36 drops below a negative threshold, the parasitic junction of the transistor starts conducting, so there is a limit to the allowed input voltage range. The transistor then functions as the shorting switch, so that the shorting switch itself and the low pass filter together implement the desired high pass filter functionality.

The switch is closed when a high frequency component is detected in this example. This means the protection is always active even when the user makes a mistake when applying the voltages. This also means the two sensors may be used quasi-simultaneously. In that case, the first sensor is muted during the high voltage pulses and not during the remaining time (which is more than 90% of the time).

An alternative is to actively look for the DC drive component of the first sensor 14 and only open the switch 32 when this DC signal is present, if the second sensor signals have no such DC component.

This device enables two sensors that make use of different voltages and frequencies to be driven by a shared pair of connection wires 16, with automatic selection of the suitable sensor. The first sensor 14 is shorted to protect it from the signals that result from the use of the second sensor 15.

The low voltage first sensor circuit 31 for example uses a switching frequency for the current modulation in the kHz range, such as 200 kHz, and a low voltage line voltage such as 200 mV.

The supply voltage present during pressure sensing is for example about 2.5V. The switch is open during pressure reading unless there is a presence of a high voltage on the supply (with a detection level of 2.5V plus a threshold voltage). The current is modulated from the pressure reading circuit. Across the resistor (R1 or R2), the resulting voltage will be modulated accordingly, for example with an amplitude of around 200 mV.

The high voltage second sensor (the ultrasound-based flow sensor) involves high frequencies and high voltages such as 10 MHz and 10 V signals.

The low pass filter 34 may be implemented using passive components such as resistors and capacitors. These components can tolerate high voltage signals when selected properly. The cut-off frequency of the low pass filter may be chosen close to or slightly above the frequency used in the low voltage sensor circuit e.g. 200 kHz. Therefore, the filter can follow the signals generated by the low voltage sensor readout circuit but it cannot follow the stimulus signals of the flow sensor transducer.

As mentioned above, if the existence of a DC voltage is sufficient to prove that the first sensor is active and the second sensor is not, then a low cut-off frequency may be used to just look for the DC drive signal. However, if a DC voltage is present for example while stimulating the second sensor, it is then necessary to switch off the first sensor while the DC signal is still present. If the cut-off frequency is much lower than 200 kHz, then the pressure sensor signal could trigger the switch to become conductive hereby turning off the pressure circuit itself. This will only happen when the signal amplitude is relatively large.

Note that realizing a low cut-off frequency takes more silicon area than a higher cut-off frequency. Having a cut-off frequency of 200 kHz is good enough with respect to the high frequency signals of the Doppler sensor.

Figure 4:
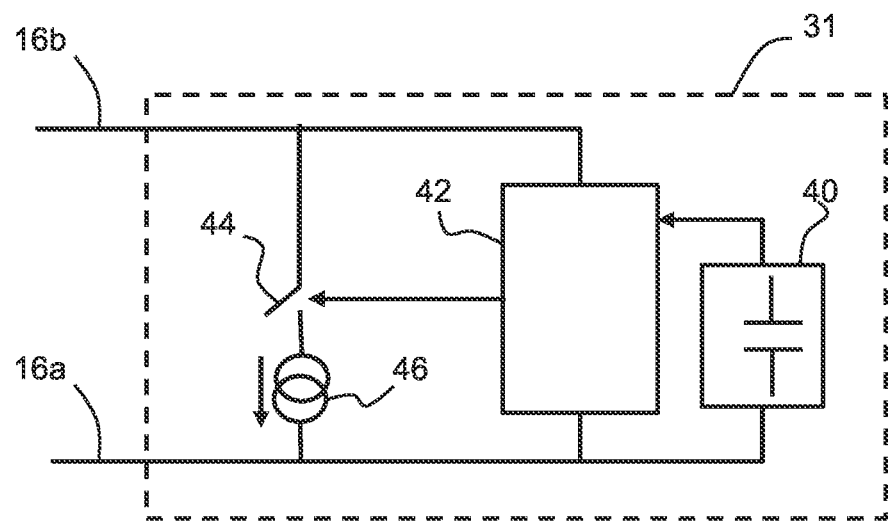
FIG. 4 shows an example implementation of a low voltage sensor readout circuit.

An example implementation of the low voltage sensor readout circuit 31 is shown in FIG. 4. The circuit connects to the two interface wires 16. One wire 16a provides the ground potential and the other wire 16b provides the supply voltage (e.g. 2.5V) and carries the sensor output signal. For robust sensing, it is preferred to have the output signal digitally coded or frequency modulated. For this purpose, the sensor 40 is coupled to a modulation circuit 42 that controls pulse width modulation of a modulation switch 44. The switch controls the coupling of a current source 46 between the wires 16. The coded output signal modulates the supply current that can be sensed at the proximal sensor control system 10.

Figure 5:
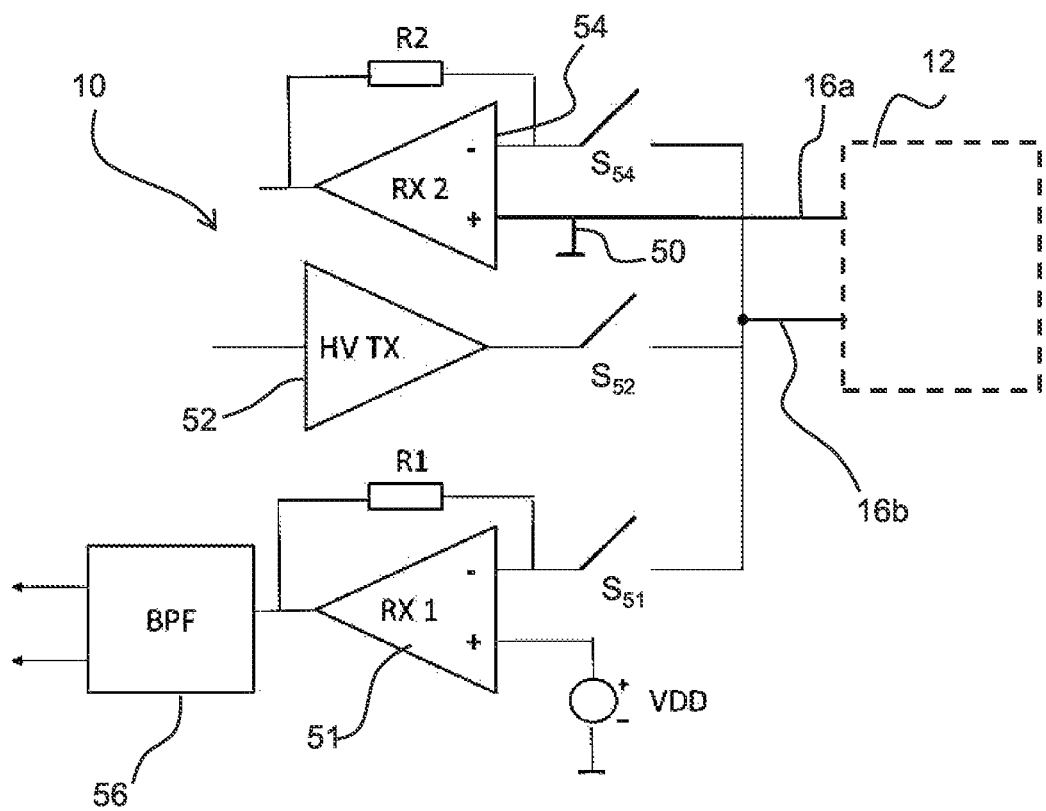
FIG. 5 shows an example implementation of a control system at the proximal end of the shaft.

An example implementation of the control system 10 is shown in FIG. 5. The circuit connects to the shaft 12 by the two wires 16a, 16b. The sensor control system 10 comprises a ground connection 50 for a first one 16a of the pair of electrical wires.

A first readout amplifier 51 is provided for reading out a modulated current on the second 16b of the pair of electrical wires and for providing a DC voltage on the second of the pair of electrical wires. For this purpose, it comprises an operational amplifier having its positive input connected to a reference DC voltage source VDD, which provides the DC voltage in the first range.

The first range is for example 1 V to 10 V, such as 1 V to 5 V, for example 2.5 V.

The current to be sensed is received at the inverting input, and a resistive feedback of resistor R1 implements a current integrator.

A driving unit 52 is for providing a drive voltage on the second of the pair of electrical wires for the second sensor, and thus in the second frequency range. This is typically the MHz frequency range. The second range is for example >100 kHz, or >1 MHz for example.

In one arrangement, the DC voltage of the amplifier 51 is not provided simultaneously with providing the stimulus from the driving unit 52, so that $S_{51}$ and $S_{52}$ do not conduct simultaneously. However, it may instead be possible to have a DC voltage as well as stimulating the driving unit 52. For this purpose, both units 51 and 52 could be coupled capacitively to wire 16b and a separate supply voltage could be added (e.g. via inductive coils).

A second readout amplifier 54 is provided for reading out a sensor signal on the second of the pair of electrical wires in the second frequency range. The current flowing may again be measured using a current sense amplifier, in the form of an operational amplifier with a feedback resistor R2.

The connection between the two readout amplifiers and the driving unit to the second wire 16b is controlled by respective switches $S_{51}$, $S_{52}$, $S_{54}$.

In this arrangement, the wire $16_a$ provides a ground potential. The other wire 16b transfers all signals to and from the two sensors.

The switches may be controlled to implement use of one sensor at a time, or alternatively the DC voltage may be provided continuously. The flow sensor and pressure sensor could for example work quasi-simultaneously with a pressure reading between the flow pulses.

When the switch $S_{52}$ is conductive the system is in flow transmit mode and capable of transmitting stimulus pulses, generated by the amplifier 52 to the second sensor 15. In some arrangements, when switch $S_{52}$ is conductive, the other two switches $S_{51}$ and $S_{54}$ are not conductive.

When switch $S_{54}$ is conductive, switch $S_{51}$ is non-conductive and the system is capable of receiving the (weak) echo signals coming from the flow sensor 15.

When switch $S_{51}$ is conductive, the system provides the supply voltage VDD to the wire that is used to supply the pressure sensor read-out circuit. The same readout amplifier 51 also receives signals from the sensor 14 as a modulated current. It may also be possible to pick up signals from the flow sensor 15 at the same time since they are in a different frequency domain.

In particular, when the high voltage flow sensor is active, the pressure sensor must be protected. When these high voltage signals are present, the pressure sensor indeed will not be operational, but when receiving the signal back from the flow sensor (with the high voltage actuation pulse signals no longer present), the pressure sensor can be already made active. In this way, it is also possible to receive signals from both amplifiers 54 and 51.

The first readout amplifier may further comprise a filter 56 (a low pass filter or a band pass filter) for selecting signals of the first sensor 14. Thus, even if a response of the second sensor is picked up, it can be filtered out.

Figure 6:
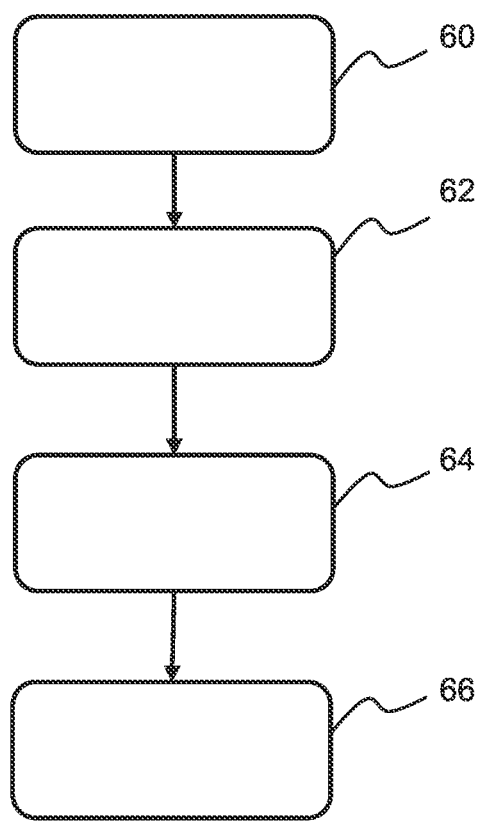
FIG. 6 shows a method of controlling a sensor device.

FIG. 6 shows a method of controlling a sensor device, the sensor device comprising a shaft 12, a pair of electrical wires 16 running along the shaft and a sensing head at a distal end of the shaft connected to the pair of electrical wires.

In step 60, a first sensor of the sensor head is operated, resulting in signals carried by the pair of electrical wires in a first frequency range and a first voltage range. These signals may be a DC drive voltage having relatively low voltage level (e.g. less than 10 V, for example less than 5 V). There may also be a modulated current signal, which may have a non-DC component for example in the kHz range.

In step 62, a second sensor of the sensor head is operated resulting in signals carried by the pair of electrical wires in a second frequency range and a second voltage range. These signals are for example AC voltage pulses in the MHz range and with voltages above 5 V, for example above 10 V.

In step 64, the first sensor is shorted based on frequency and/or voltage level, thereby to prevent the first sensor being exposed to the signals associated with the second sensor, in particular the high voltage signals which may damage the first sensor.

In step 66, the signals are received back from both sensors. This can be at the same time or sequentially (so that step 66 may be distributed between steps 60 and 62).

In this method, a frequency-based control is used to short the first sensor so that it is not exposed to the (higher voltage) signals of the second sensor.

The examples above show a single high voltage sensor and a single low voltage sensor. They may be multiple sensors of one or both types, for example multiple low voltage sensor in parallel, each of which is shorted when the normal DC drive level is not present.

The example above has the shorting switch actively closed by the presence of the high voltage and/or high frequency signal. The opposite is possible where the switch is actively opened by the presence of a low voltage and/or low frequency i.e. DC signal.

The examples of flow sensing and pressure sensing have been discussed above. The invention may however be used for any types of sensor that have different frequency characteristics for the signals that are present during use of the sensors.

The invention is for example applicable to sensors that require a high voltage bi-polar voltage (typically a flow-sensor or a single element imaging sensor, e.g. a beacon for navigation purposes) in combination with a second sensor that is controlled by a ASIC that operates the second sensor using low voltages or unipolar high voltages (e.g. sensors that measure physiological parameters such as temperature, pressure, glucose concentration, or local pH).

Some of the examples above assume that one sensor has no DC component and the other has a significant DC component. However, by detecting frequencies in other bands, sensors that differ in other frequency bands (instead of at or near DC) may be distinguished from each other. The invention is particularly applicable for signals that are by nature bipolar, while ASICs in the catheter tip operate at unidirectional potentials.

The invention can be applied to all catheter-like sensing products.

The invention is described above as based primarily on frequency separation of the two signal types. However, as also explained above, voltage thresholds may also be used, for example to distinguish between low voltage high frequency components (which may be from either sensor) and high voltage high frequency components (which are for example unique to the driving pulses of the second sensor).

The separation may also be based on voltage only, so that only the high voltage of the driving pulses of the second sensor are used to activate the shorting circuit.

Different approaches are possible based on the desired circuit complexity versus reliability of detection and control.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:
1. An apparatus, comprising:
   a catheter or guidewire;
   a first sensor type positioned at a distal portion of the catheter or guidewire;
   a different, second sensor type positioned at the distal portion of the catheter or guidewire;

a first electrical wire and a second electrical wire extending along the catheter or guidewire, wherein at least one of the first electrical wire or the second electrical wire is configured to carry:
  a plurality of first signals associated with the first sensor type and comprising a first voltage range; and
  a plurality of second signals associated with the second sensor type and comprising a different, second voltage range; and
a shorting circuit configured to short the first sensor type based on at least voltage to prevent the first sensor type being exposed to the plurality of second signals associated with the second sensor type, wherein the shorting circuit comprises:
  a shorting switch; and
  a filter circuit configured to close the shorting switch when the plurality of second signals in the second voltage range are present on at least one of the first electrical wire or the second electrical wire.

2. The apparatus of claim 1, wherein the first sensor type comprises a pressure sensor.

3. The apparatus of claim 2, wherein the second sensor type comprises a flow sensor.

4. The apparatus of claim 3, wherein the flow sensor comprises an ultrasound transducer.

5. The apparatus of claim 1, wherein the second voltage range is higher than the first voltage range.

6. The apparatus of claim 1, wherein the first electrical wire is configured to carry a ground signal such that the second electrical wire is configured to carry the plurality of first signals and the plurality of second signals.

7. The apparatus of claim 1, wherein the filter circuit is configured to open the shorting switch when the plurality of second signals in the second voltage range are not present on at least one of the first electrical wire or the second electrical wire.

8. The apparatus of claim 1, wherein the shorting circuit is configured to:
  perform a comparison between:
    a voltage present on at least one of the first electrical wire or the second electrical wire; and
    the voltage after the filter circuit; and
  close the shorting switch based on the comparison.

9. The apparatus of claim 8, wherein, to perform the comparison, the shorting circuit is configured to:
  determine a difference between:
    the voltage present on at least one of the first electrical wire or the second electrical wire; and
    the voltage after the filter circuit; and
  compare the difference to a threshold amount.

10. The apparatus of claim 1,
  wherein the shorting circuit comprises a comparator and a resistor,
  wherein the comparator is positioned between the shorting switch and the resistor, and
  wherein an output of the comparator is configured to close the shorting switch when a voltage after the resistor is greater than the voltage after the filter circuit by more than a threshold amount.

11. The apparatus of claim 10, wherein the filter circuit comprises a low pass filter.

12. The apparatus of claim 1,
  wherein the plurality of first signals comprises a first frequency range and the plurality of second signals comprises a different, second frequency range, and
  wherein the shorting circuit configured to short the first sensor type based on both frequency and the voltage.

* * * * *